(12) United States Patent
Poncon et al.

(10) Patent No.: US 10,258,540 B2
(45) Date of Patent: Apr. 16, 2019

(54) ADAPTOR FOR A DRUG DELIVERY DEVICE AND METHOD FOR MOUNTING SAID ADAPTOR THEREON

(71) Applicant: Becton Dickinson France, Le Pont de Claix (FR)

(72) Inventors: Gilbert Poncon, Pommiers la Placette (FR); Guillaume Grunhut, Grenoble (FR)

(73) Assignee: Becton Dickinson France, Le Pont de Claix (FR)

( * ) Notice: Subject to any disclaimer, the term of this patent is extended or adjusted under 35 U.S.C. 154(b) by 582 days.

(21) Appl. No.: 14/905,063

(22) PCT Filed: Jul. 11, 2014

(86) PCT No.: PCT/EP2014/064947
§ 371 (c)(1),
(2) Date: Jan. 14, 2016

(87) PCT Pub. No.: WO2015/007650
PCT Pub. Date: Jan. 22, 2015

(65) Prior Publication Data
US 2016/0143811 A1    May 26, 2016

(30) Foreign Application Priority Data

Jul. 15, 2013 (EP) ..................... 13306009

(51) Int. Cl.
*A61J 1/20* (2006.01)
*A61M 5/34* (2006.01)
(Continued)

(52) U.S. Cl.
CPC ............... *A61J 1/2048* (2015.05); *A61J 1/18* (2013.01); *A61J 1/2096* (2013.01); *A61M 5/344* (2013.01);
(Continued)

(58) Field of Classification Search
CPC .......... A61J 1/2048; A61J 1/18; A61J 1/2096; A61M 5/344; A61M 39/10; A61M 2039/1077
See application file for complete search history.

(56) References Cited

U.S. PATENT DOCUMENTS 4,895,570 A   1/1990   Larkin
5,624,402 A   4/1997   Imbert
(Continued)

FOREIGN PATENT DOCUMENTS

EP   1034810 B1   7/2005
EP   1600190 B1   8/2007
(Continued)

*Primary Examiner* — Philip R Wiest
(74) *Attorney, Agent, or Firm* — The Webb Law Firm (57) ABSTRACT

An adaptor intended to be mounted on a distal tip of a drug delivery device is provided. The distal tip defines an axial passageway for transfer of a product contained in the drug delivery device. The adaptor has a longitudinal axis A aligned on the axial passageway. The adaptor includes: a connection member for connecting the adaptor to a connector; an inner ring releasably engageable on the distal tip; and a compression component separate from the inner ring and configured to be unreleasably snap-fitted onto the inner ring engaged on the distal tip by proximal movement of the compression component with respect to the inner ring. The compression component is configured to exert a centripetal pressure on the inner ring so as to prevent axial movement of the inner ring with respect to the distal tip.

14 Claims, 3 Drawing Sheets

(51) Int. Cl.
*A61M 39/10* (2006.01)
*A61J 1/18* (2006.01)

(52) U.S. Cl.
CPC ..... *A61M 39/10* (2013.01); *A61M 2039/1077* (2013.01)

(56) References Cited

U.S. PATENT DOCUMENTS

| | | | |
|---|---|---|---|
| 5,833,275 | A | 11/1998 | Andersen |
| 6,491,665 | B1 | 12/2002 | Vetter et al. |
| 6,520,935 | B1 | 2/2003 | Jansen et al. |
| 7,648,481 | B2 | 1/2010 | Geiger et al. |
| 7,806,861 | B2 | 10/2010 | Witowski |
| 2003/0163093 | A1* | 8/2003 | Thibault ............... A61M 5/344 604/241 |
| 2006/0033331 | A1 | 2/2006 | Ziman |
| 2010/0176584 | A1 | 7/2010 | Ito et al. |
| 2011/0130717 | A1 | 6/2011 | David et al. |
| 2012/0157928 | A1 | 6/2012 | Mermet |
| 2012/0179108 | A1 | 7/2012 | Delabie |
| 2013/0338603 | A1 | 12/2013 | Roedle et al. |
| 2013/0338604 | A1 | 12/2013 | Roedle |
| 2014/0012204 | A1 | 1/2014 | Bosshardt et al. |
| 2014/0039408 | A1 | 2/2014 | Perot et al. |
| 2014/0142553 | A1 | 5/2014 | Poncon |
| 2015/0238703 | A1 | 8/2015 | Glocker |
| 2015/0283372 | A1 | 10/2015 | Maritan et al. |
| 2016/0250415 | A1 | 9/2016 | Yagi et al. |

FOREIGN PATENT DOCUMENTS

| | | | | |
|---|---|---|---|---|
| EP | 2182265 | A1 | 5/2010 | |
| EP | 2510964 | A1 | 10/2012 | |
| FR | 2809316 | A1 | 11/2001 | |
| WO | 9720587 | A1 | 6/1997 | |
| WO | WO 99/44661 | * | 3/1998 | ............. A61M 5/50 |
| WO | 9944661 | | 9/1999 | |
| WO | 2006087763 | A1 | 8/2006 | |
| WO | 2007051655 | A1 | 5/2007 | |
| WO | 2008153019 | A1 | 12/2008 | |
| WO | 2009144583 | A1 | 12/2009 | |
| WO | 2010140019 | A1 | 12/2010 | |
| WO | 2010150042 | A1 | 12/2010 | |
| WO | 2012049532 | A1 | 4/2012 | |
| WO | 2012116790 | A1 | 9/2012 | |
| WO | 2012116791 | A1 | 9/2012 | |
| WO | 2013010953 | A1 | 1/2013 | |
| WO | 2014057071 | A1 | 4/2014 | |
| WO | 2014072440 | A1 | 5/2014 | |
| WO | 2014086437 | A1 | 6/2014 | |

* cited by examiner

ADAPTOR FOR A DRUG DELIVERY DEVICE AND METHOD FOR MOUNTING SAID ADAPTOR THEREON

CROSS-REFERENCE TO RELATED APPLICATIONS

This application is the United States national phase of International Application No. PCT/EP2014/064947 filed Jul. 11, 2014, and claims priority to European Patent Application No. 13306009.5 filed Jul. 15, 2013, the disclosures of which are hereby incorporated in their entirety by reference.

BACKGROUND OF THE INVENTION

Field of the Invention

The present invention relates to an improved adaptor, for example a luer lock adaptor, for use with a drug delivery device. The adaptor allows a safe connection between the drug delivery device and a connector to be coupled to the drug delivery device. The invention also relates to a drug delivery device provided with such an improved adaptor, to a method for mounting said adaptor on such a drug delivery device, and to an assembly comprising such an improved adaptor and a connector connected to said adaptor.

Description of Related Art

Various medical devices are known for transferring and/or storing medical fluids, such drug delivery devices, as syringes, needle assemblies, perfusion devices, transfusion devices and connectors such as for example IV (Intra Venous), IM (Intra Muscular), subcutaneous connectors. It is essential for safety reasons that these various medical devices can be assembled together correctly and securely. The use of specific adaptors between the various medical devices allows them to be assembled, ensuring a sealed connection and providing protection against the contamination of the medical liquid products they contain.

A conventional drug delivery device usually comprises a hollow body forming a container for a medical product. The distal end of the body forming the container usually comprises a tip in which an axial passageway is arranged and through which said medical product is expelled from the container. When the medical product needs to be transferred from the drug delivery device to a connector, the connection between the drug delivery device and the connector is usually completed thanks to an adaptor. The adaptor is usually mounted on the distal tip of the drug delivery device and allows the transfer of medical product from the drug delivery device to the connector.

Usually, an adaptor intended to be mounted on the distal tip of a drug delivery device comprises a collar fixed to the drug delivery device and surrounding said distal tip, said collar comprising means for connecting the connector to the adaptor, and therefore to the drug delivery device. A luer lock adaptor is such a collar further provided with locking means, such as a thread capable of cooperating with a corresponding thread locating on the connector, so that the connection between the connector and the drug delivery device via the adaptor is optimized.

Conventional drug delivery devices typically are made of plastic or glass. Glass barrels are used for medications that are particularly susceptible to interact with ambient gases or with the container material(s). Glass barrels are also preferably used for medications that are pre-filled into the barrel and stored over a considerable period of time prior to use. When the drug delivery device and its distal tip are made of plastic material, the adaptor may be molded together with the distal tip, using the same material or one of a kind. Anyway, because of difficulty of manufacturing, glass barrels and glass distal tips in particular may require a separately formed adaptor to be mounted thereon. The adaptor should be securely mounted onto the distal tip of the drug delivery device to avoid its disconnection from the tip.

Usually, the adaptors are first mounted on the distal tip of the drug delivery device by friction force and the connector is then mounted on the free end of the adaptor, for example by screwing. In general, adaptors are provided with a radially expandable ring which is friction forced on the distal tip. The adaptor is then intended to remain immobile with respect to the distal tip by slip fit interengagement and by virtue of the friction force exerted by the ring on the distal tip.

The strength of the assembling of the adaptor on the distal tip of the drug delivery device depends firstly on the accuracy of the dimensions of the external surface of both the distal tip and the adaptor, secondly on the force used to engage the adaptor on the distal tip. Due to industrial tolerances, the assembling of the adaptor on the distal tip is therefore rather inaccurate and the strength of the assembling cannot be always guaranteed. It may then occur that such interengagement is not secured enough, the result being that the adaptor may be movable by rotation and/or removable by translational movement with respect to the distal tip. The connection between the drug delivery device and the connector is therefore neither stabilized nor safe.

SUMMARY OF THE INVENTION

Therefore, there is a need for an improved adaptor enabling to ensure a reliable assembling of the adaptor onto a drug delivery device. There is also a need of a drug delivery device provided with such an adaptor.

Medical uses require specific assembling conditions to ensure that the drug delivery device is not contaminated. A suitable quality level is obtained by performing the assembling in clean rooms, under a specific grade, in which the drug delivery devices are washed, then siliconized to allow a better gliding of the stopper. However, the friction force connection of an adaptor onto the distal tip of a drug delivery device may be highly impacted by the presence of silicone that may inadvertently be applied on the outside surface of the distal tip.

There is therefore a need for an improved adaptor enabling a reliable assembling on the distal tip of a drug injection device. There is also a need of a drug delivery device provided with such an adaptor.

Other problems have been reported concerning the use of adaptors with various drug delivery devices. Indeed, most of the adaptors that are available for use in the medical field for the purpose of connecting drug delivery devices with connectors are made of plastic material. The capability of deformation of such plastic material is influenced by aging and temperature conditions. In addition, plastic materials are sensitive to sterilization process.

Indeed, the range of available plastic material usable in the medical field is limited in term of composition and color.

In addition, it may happen that, for example after a certain time or after having been submitted to specific conditions like sterilization cycles and/or submission to different temperatures, elastic characteristics of the plastic material chosen are modified. As a consequence, the adaptor does not remain immobile with respect to the distal tip of the drug delivery device. Parts of the adaptor may be weakened by sterilization and may no longer ensure a sufficient tightening onto the distal tip, leading to an easy disconnection of the adaptor. Also, it may happen that the friction forces are not important enough to prevent the adaptor from rotating with respect to the distal tip, particularly when the user tries to screw a connector on to the adaptor. It is therefore impossible for the user to determine whether the connector is well fitted in the adaptor or not and, as a consequence, whether the connector is well connected to the distal tip of the drug delivery device. An incorrect connection between the drug delivery device and the connector may cause the displacement of the adaptor and/or of the connector in regards to the drug delivery device, that could lead to product leakage and therefore incorrect doses administered to the patient as well as product waste. To overcome this problem and ensure right connection between the connector and the adaptor, when screwing the connector onto the adaptor, the user tends to hold the drug delivery device by the adaptor itself. The adaptor having a small size, it may be difficult to handle it efficiently. During this operation, the user's fingers are close to the tip of the injection drug delivery device and to the axial passageway, increasing the risk of contamination of the medical liquid contained.

There is therefore a need for an improved adaptor enabling the use of a wider range of material while ensuring an efficient and reliable connection between the drug delivery device and the connector. There is also a need of a drug delivery device provided with such an adaptor.

An aspect of the present invention is an adaptor intended to be mounted on the distal tip of a drug delivery device, allowing a safe connection between the drug delivery device and a connector intended to be connected onto the adaptor. In particular, the adaptor of the invention comprises means for ensuring an optimal fixation of the adaptor onto the distal tip, so that said adaptor may not be disconnected from the distal tip in use.

A first aspect of the invention is an adaptor intended to be mounted on a distal tip of a drug delivery device, said distal tip defining an axial passageway for the transfer of a product contained in said drug delivery device, said adaptor having a longitudinal axis A aligned on said axial passageway, the adaptor comprising connecting means for connecting said adaptor to a connector, said adaptor further comprising:
  an inner ring releasably engageable on said distal tip,
  compressing means, separate from said inner ring and intended to be unreleasably snap-fitted onto said inner ring engaged on said distal tip by proximal movement of said compressing means with respect to said inner ring, said compressing means thereby exerting a centripetal pressure on said inner ring so as to prevent axial movement of said inner ring with respect to said distal tip.

The adaptor of the invention may be used in particular for connecting a connector to a drug delivery device.

The risks of the adaptor of the invention being displaced and eventually misplaced on the distal tip of the drug delivery device it is intended to be mounted onto are therefore greatly limited. The adaptor of the invention therefore allows a reproducible connection of a connector to a drug delivery device and ensures that the connector is correctly positioned with respect to the drug delivery device.

Indeed, in the adaptor of the invention, the fastening of the adaptor onto the distal tip does not rely on a simple friction force between an expandable ring and the distal tip like in the prior art, but on a specific radial inward force, actually the centripetal pressure exerted by the compressing means or compression component. The global friction force exerted on the distal tip is therefore increased, and the adaptor is securely attached to the distal tip, with no risk of detachment therefrom. In addition, as it will appear from the description below, the force required by the user to position the adaptor is to be applied in two steps. The right positioning of the adaptor is therefore facilitated and simple, and the risk to break the distal tip at the time the adaptor is mounted thereon is reduced.

In the present application, "user" means a healthcare worker who may need to use the adaptor of the invention in order to connect thereon a connector such as an IV line, or alternatively it may be the drug delivery device manufacturer who will perform the mounting of the adaptor of the invention onto the distal tip of a drug delivery device, so as to provide the drug delivery device with the adaptor already mounted thereon. In such case, the mounting step may further comprise the connection of a cap on the adaptor for ensuring safe closure of the drug delivery device in its storage position while there is no connector connected thereon. The mounting step at the manufacturer's premises may be completed automatically on assembly lines.

As a consequence, in the present application, "connector" means any device intended to be connected to the adaptor, either for allowing the transfer of a product from the drug delivery device to another medical device, such as a needle hub, a pocket drip, a vial, an IV (Intra Venous) line, an IM (Intra Muscular) line, or on the contrary for safely closing the filled drug delivery device before its use and for preventing any contamination, like for example a closure cap in the storage position of the drug delivery device. Such a connector is provided with a connecting means or connector connection member capable of cooperating with the connecting means or connection member present on the adaptor of the invention.

As mentioned above, the adaptor of the invention is mounted onto the distal tip in two steps. The inner ring is first engaged on the distal tip. This step does not require a high force to be produced by the user. Once the inner ring is positioned on the distal tip, the user then moves the compressing means proximally towards the inner ring so as to snap-fit it thereon. Here again, this step does not require that a high force be applied by the user. The integrity of the distal tip is therefore preserved. The adaptor of the invention therefore allows a safe connection of the adaptor to the distal tip, even if the distal tip is made of glass.

Once mounted, with the inner ring locked in translation with respect to the distal tip by means of the unreleasablly snap-fitted compressing means, the adaptor may not be disconnected from the distal tip without breaking and damaging the whole assembly.

For example, the presence of the compressing means of the adaptor of the invention also allows preventing the inner ring, and consequently the adaptor, from rotating with respect to the distal tip. In embodiments, some locking means may be formed on a proximal outer surface of the distal tip, preferably aligned on the longitudinal axis of the drug delivery device, for further preventing rotation of the adaptor with respect to the distal tip.

In one embodiment, the adaptor of the invention may be used with a conventional conical distal tip made of glass material without requiring that the shape or the outer surface of said distal tip be modified, for example by providing it with an annular groove or an annular ridge.

In another embodiment, said inner ring comprises a circular wall capable of being outwardly radially expanded under a pressure exerted radially outwardly on an inner face of said circular wall, and capable of being inwardly radially compressed under a pressure exerted radially inwardly on an outer face of said circular wall, said compressing means comprise an outer ring capable of receiving at least partly said inner ring, said outer ring comprising an inner radial rim capable of exerting a centripetal pressure on said outer face of said circular wall when said compressing means is snap-fitted onto said inner ring. The radial inward force exerted by the compressing means is therefore well distributed along the circumference of the distal tip, and the fixation is ensured, thereby preventing any rotational and/or translational movement of the adaptor with respect to the distal tip.

The inner radial rim of the outer ring provides additional rigidity and enhanced mechanical property to the part of the outer ring intended to be in contact with the inner ring in order to exert an optimal centripetal pressure on said inner ring.

In one embodiment, said circular wall is provided with a longitudinal cut along a portion of its circumference, said longitudinal cut extending from a proximal end to a distal end of said circular wall. The longitudinal cut provides the circular wall with both said capacities of radial expansion and radial compression. In embodiments, said portion of circumference is wide enough for defining an empty space between two longitudinal edges of said longitudinal cut, when no pressure is exerted on said circular wall. In particular, the portion of the circumference along which the circular wall is cut is wide enough so that the inner diameter of the circular wall is reduced when the circular wall is radially compressed, for example up until the two longitudinal edges of the cut contact each other. On the contrary, the inner diameter of the circular wall is increased when a radial outward pressure is exerted on the inner face of the circular wall, the two longitudinal edges of the cut thereby moving away from each other. For example, said portion of circumference is at least 2 mm wide. The longitudinal cut of the circular wall facilitates the mounting of the inner ring onto the distal tip of the drug delivery device it is intended to be mounted on.

In another embodiment, said circular wall is provided with a distal annular outer rim capable of cooperating with said inner radial rim for unreleasably snap-fitting said compressing means onto said inner ring.

In yet another embodiment, said connecting means are located on the compressing means. An appropriate assembly of the connector with the drug delivery device may thus be completed. For example, the connecting means comprises a thread provided on an inner wall of said outer ring. In such a case, the connector is provided with a corresponding thread for engagement with the thread provided on the outer ring.

Another aspect of the present invention is a drug delivery device comprising a distal tip defining an axial passage-way for the transfer of a product contained in said drug delivery device, characterized in that it further comprises at least one adaptor as previously described.

In one embodiment, the distal tip is made of glass.

In another embodiment, the distal tip is conical and distally tapered.

In yet another embodiment, the distal tip is provided with an annular groove capable of receiving said inner ring when said inner ring is engaged on said distal tip. The annular groove forms an additional obstacle to the potential detachment of the adaptor from the distal tip, once the adaptor is mounted on said distal tip.

In yet another embodiment, a proximal region of the outer surface of the distal tip is provided with additional locking means intended to cooperate with the inner ring so as to prevent the rotation of said adaptor with respect to said distal tip when the adaptor is mounted on said distal tip.

Another aspect of the present invention is a method for mounting an adaptor as previously described on the distal tip of a drug delivery device as described above, said method comprising at least the following steps:
  slidingly engaging the inner ring onto the distal tip,
  snap-fitting the compressing means onto the inner ring by proximal movement of said compressing means with respect to said inner ring.

In one embodiment where the distal tip is provided with an annular groove, the inner ring is slidingly engaged on the distal tip until it is received into said annular groove.

Another aspect of the invention is an assembly comprising an adaptor as described above and a connector connected to said adaptor. In embodiments, the assembly further comprises tamper evidence means of the removal of the connector from the adaptor. For example, when the connector is a closure cap connected to the adaptor in view of closing a prefilled drug delivery device in a storage position, a tearable label may be stuck bridging a part of the adaptor and a part of the closure cap so as to constitute tamper evidence means of a fraudulous removal of the closure cap from the adaptor before use of the drug delivery device.

BRIEF DESCRIPTION OF THE DRAWINGS

The invention and the advantages arising therefrom will clearly emerge from the detailed description that is given below with reference to the appended drawings in which.

DESCRIPTION OF THE INVENTION

In this application, the distal end of a component or of a device is to be understood as meaning the end furthest from the user's hand and the proximal end is to be understood as meaning the end closest to the user's hand. Likewise, in this application, the "distal direction" is to be understood as meaning the direction of injection, with respect to the drug delivery device the adaptor of the invention is intended to be mounted on, and the "proximal direction" is to be understood as meaning the opposite direction to said direction of injection.

With reference to FIGS. 1-3B, is shown an adaptor 10 of the invention, comprising a first component, an inner ring 20, and a separate second component, an outer ring 30. The adaptor 10 is intended to be mounted on a drug delivery device 1 comprising a barrel 5 and provided at its distal end with a distal tip 2 (see FIG. 4) in order to allow connection of a connector (not shown) to the drug delivery device 1 via the adaptor 10.

The connector intended to be connected to the drug delivery device 1 thanks to the adaptor 10 of the invention may be any device capable of being connected to the adaptor 10, either for allowing the transfer of a product from the drug delivery device 1 to another medical device, such as a needle hub, a pocket drip, a vial, an IV (Intra Venous) line, an IM (Intra Muscular) line, or on the contrary for safely closing the filled drug delivery device 1 before its use and for preventing any contamination, like for example a closure cap 40 in the storage position of the drug delivery device (as will be shown on FIGS. 4-7). In the example shown, the connector is intended to be provided with a connecting means or connector connection member, such as a thread, capable of cooperating with a corresponding connecting means or connection member, for example thread 34 (see FIG. 3A), located on the adaptor 10, as will be explained below.

With reference to FIGS. 1-3B, the first component or inner ring 20 comprises a circular wall 21 provided at its distal end with an annular outer rim 22 having a distally tapered outer face 22a. The circular wall 21 is provided with a longitudinal cut 23 along a portion of its circumference, said portion of circumference separating the two longitudinal edges (23a, 23b) of the longitudinal cut 23, and thereby defining an empty space between these two longitudinal edges (23a, 23b) when no pressure is exerted on said circular wall 21. The longitudinal cut 23 extends along the whole height of the circular wall 21. The presence of the longitudinal cut 23 defining said empty space confers to the circular wall 21, and therefore to the inner ring 20, a capacity for radial expansion and a capacity for radial compression. On FIG. 2A, the circular wall 21 is shown in a rest position. Anyway, the circular wall 21 is deformable under a pressure exerted radially outwardly on its inner face 21c, in which case the inner diameter of the circular wall 21 increases under the deformation caused, the two longitudinal edges (23a, 23b) of the longitudinal cut 23 moving away from each other. In addition, the circular wall 21 is deformable under a pressure exerted radially inwardly on its outer face 21d, in which case the inner diameter of the circular wall 21 decreases under the deformation caused. In particular, the portion of the circumference along which the circular wall 21 is cut is wide enough, for example at least 2 mm wide, so that the inner diameter of the circular wall 21 is reduced when the circular wall 21 is radially compressed, for example up until the two longitudinal edges (23a, 23b) of the cut 23 contact each other. Due to the presence of the longitudinal cut 23 defining an empty space along the circumference of the circular wall 21, the two longitudinal edges (23a, 23b) do not come in contact with each other when the circular wall is in its rest position. On the contrary, these two longitudinal edges (23a, 23b) may come in contact with each other when a pressure is exerted radially inwardly on the circular wall 21. The portion of circumference defining the empty space between the two longitudinal edges (23a, 23b) of the longitudinal cut 23 may be about 2 mm wide in order to provide enough elasticity to the circular wall 21 so that said circular wall 21 is capable of being alternately radially compressed or radially expanded. The circular wall 21 therefore defines a central hole 24 capable of outwardly radially expanding, and of inwardly radially shrinking depending on the nature of the pressure exerted on the circular wall 21, said central hole 24 being shaped and dimensioned in order to allow the engagement of the inner ring 20 on the distal tip 2 (see FIG. 5) of the drug delivery device 1. The first component or inner ring 20 is transitionable between a first position in which the first component or inner ring 20 is releasably engaged with the drug delivery device 1 and a second position in which the adaptor 10 is locked to the drug delivery device 1.

On the example shown, the circular wall 21 further comprises a plurality of circumferentially distributed proximal tabs 21a, separated from each other by a plurality of spaces 21b, and linked together by the annular outer rim 22. On the example shown, the circular wall 21 comprises five such proximal tabs 21a. In examples not shown, the circular wall 21 may comprise less or more of these proximal tabs 21a, such as two, three, four, six or more. The inner face 21c of these proximal tabs 21a is intended to surround the outer surface of the distal tip 2 when the inner ring 20 is engaged thereon (see FIG. 5).

On FIGS. 1-3B, the circular wall 21 is in a rest position, in other words it is in a neither expanded nor compressed state, as no pressure is exerted on its inner face 21c or on its outer face 21d.

With reference to FIGS. 1-3B, the second component or outer ring 30 comprises a circular wall 31 provided at its proximal end with an inner radial rim 32. The inner radial rim 32 of the outer ring 30 defines a central hole 33. The inner radial rim 32 is shaped and dimensioned so as to be capable of overcoming the distally tapered outer face 22a of the annular outer rim 22 of the inner ring 20. Additionally, the inner radial rim 32 is also capable of exerting a centripetal pressure on the outer face 21d of the circular wall 21 when the inner ring 20 is engaged on the distal tip 2, as shown on FIGS. 6 and 7. In particular, when the outer ring 30 is approached towards the inner ring 20 in the proximal direction during the mounting step, the inner radial rim 32 overcomes the distally tapered outer face 22a of the annular outer rim 22 and becomes engaged on the outer face 21d of the circular wall 21, thereby performing a snap-fitting connection between the outer ring 30 and the inner ring 20, as shown on FIGS. 6 and 7. In this manner, the second component or outer ring 30 is engageable with the first component or inner ring 20 to transition the first component or inner ring 20 to the second position in which the adaptor 10 is locked to the drug delivery device 1.

Figure 1:
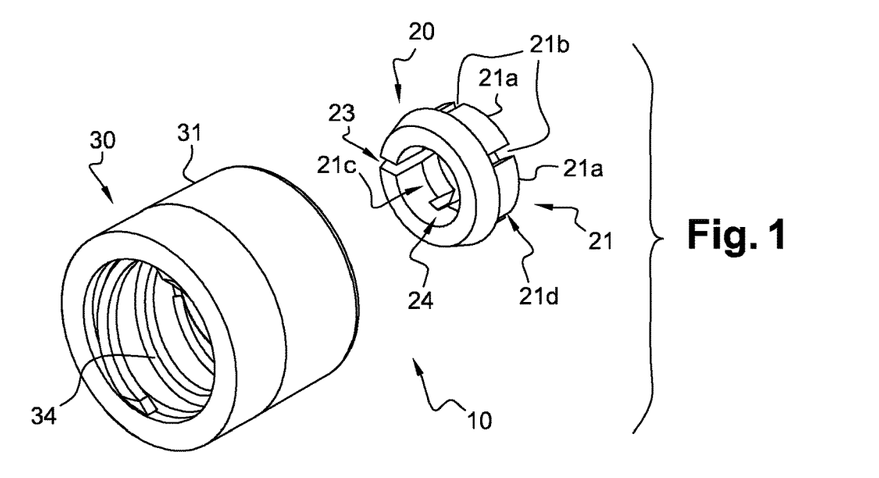
FIG. 1 is an exploded perspective view of an embodiment of the adaptor of the invention.
Figure 2A:
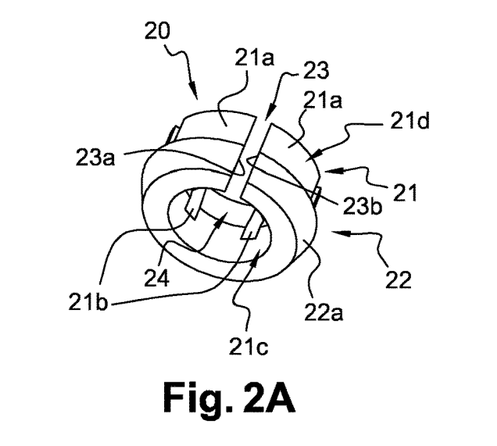
FIGS. 2A and 2B are perspective views of the inner ring of the adaptor of FIG. 1, FIGS. 3A and 3B are respectively a cross section view and a perspective view of the compressing means of the adaptor of FIG. 1.
Figure 2B:
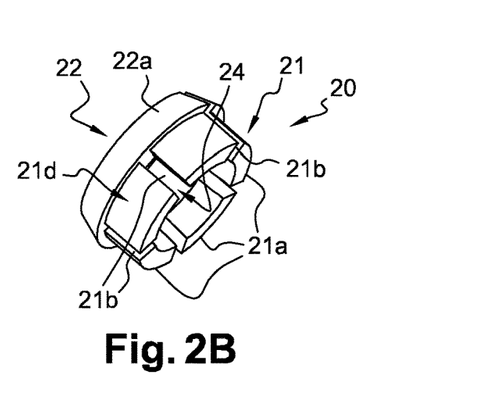
Figure 3A:
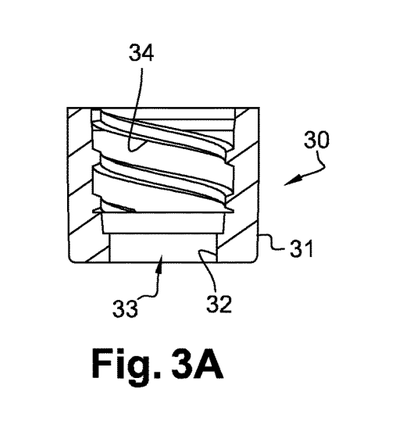
Figure 3B:
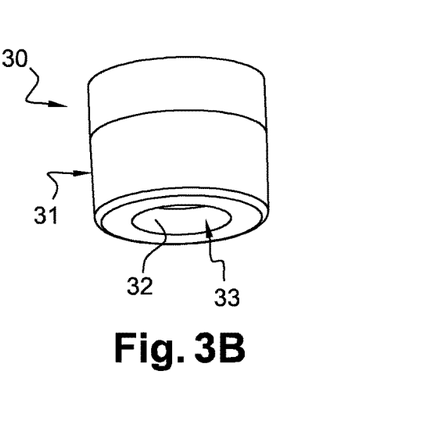

As shown on FIGS. 1 and 3A, a connection member, a thread 34, is provided on the inner face of the circular wall 31 of the outer ring 30. As it will appear from the following description, this thread 34 forms a connection member or connecting means for connecting the adaptor 10 to a connector (not shown) at the time of use of the drug delivery device 1, for example to a cap in a storage position of the prefilled drug delivery device 1.

In an embodiment not shown, the connecting means can be a groove provided on the outer face of the circular wall of the inner ring, in which a connector may be clipped. In other embodiments, the connection member or thread 34 may comprise other connection mechanisms for connecting a connector to the drug delivery device 1 via the adaptor 10. In one embodiment, the connector is connectable to the connection member or thread 34 of the adaptor 10 with the first component or inner ring 20 in the second position.

The inner ring 20 and the outer ring 30 may be made of a material selected from acrylonitrile butadiene styrene (ABS), polycarbonate (PC), polyoxymethylene (POM), polystyrene (PS), polybutylene terephthalate (PBT), polypropylene (PP), polyethylene (PE), polyamide (PA), thermoplastic elastomer (TPE) and their combinations.

Anyway, as it will appear from the description below, as the outer ring 30, and in particular its inner radial rim 32, is intended to compress inwardly radially the proximal tabs 21a of the circular wall 21 of the inner ring 20 when the adaptor 10 is mounted on the distal tip 2 (see FIG. 7), in order to prevent any axial or rotational movement of the adaptor 10 with respect to said distal tip 2, the inner radial rim 32 is preferably made from a material more rigid than the material forming the proximal tabs 21a of the circular wall 21 of the inner ring 20.

For example, in embodiments, the outer ring 30, and in particular the inner radial rim 32, is made of polyamide and the proximal tabs 21a are made of polyethylene.

In other embodiments, the outer ring 30, and in particular the inner radial rim 32, may be made of polybutylene terephthalate and the proximal tabs 21a may be made of thermoplastic elastomer.

As it will appear in the description later, the adaptor 10 is intended to be engaged on the distal tip of a drug delivery device in a two-step process (see FIGS. 5 and 6), in which the inner ring 20 is first engaged onto the distal tip 2 in a releasable way, and the outer ring 30 is then snap-fitted onto the inner ring 20 so as to axially lock it in translation with respect to the distal tip 2. The mounting of the adaptor 10 on the distal tip 2 of a drug delivery device 1 will now be described with reference to FIGS. 4-7.

Figure 4:
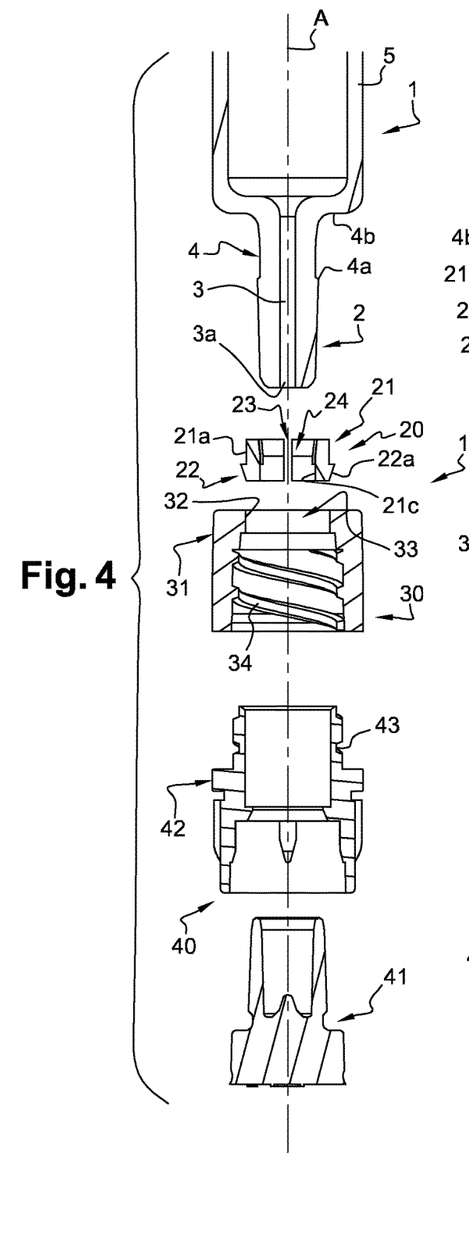
FIG. 4 is a cross section view of a drug delivery device and adaptor of the invention, before the adaptor of FIG. 1 is mounted onto the distal tip of the drug delivery device.

With reference to FIG. 4 is shown a drug delivery device 1 provided with a distal tip 2, and the adaptor 10, in a position where none of the inner ring 20 and the outer ring 30 is yet engaged on the distal tip 2.

The drug delivery device 1 and the adaptor 10 are aligned and have a common longitudinal axis A. The outer surface of the distal tip 2 is conical and distally tapered. The distal tip 2 defines an axial passageway 3 for the transfer of a product (not shown) contained or intended to be contained in the drug delivery device 1. The axial passageway 3 is open at its distal end 3a. In the example shown, the distal tip 2 is further provided with a proximal annular groove 4. The proximal annular groove 4 is defined between a distal step 4a and a proximal shoulder 4b formed by the distal part of the barrel 5 of the drug delivery device 1. For example, the outer diameter of the distal tip 2 at the location of the proximal annular groove 4 is smaller than the outer diameter of the distal tip 2 at its most distal part.

In embodiments not shown, the outer surface of the distal tip 2 may be free of any annular groove, or alternatively may be provided with an annular ridge.

The distal tip 2 may be made of plastic or glass material. In embodiments, the distal tip 2 is made of glass material. In another embodiment, the distal tip 2, as well as the drug delivery device, is made of plastic material selected from crystal clear polymer (CCP), acrylonitrile butadiene styrene (ABS), polycarbonate (PC), polystyrene (PS), polypropylene (PP), polyethylene (PE), polyamide (PA) and their combinations.

On FIG. 4 is also shown a cap 40 comprising a rubber plug 41 and a rigid sleeve 42 capable of receiving the rubber plug 41. As shown in the following description, the cap 40 is intended to close the open distal end 3a of the passageway 3 of the distal tip 2 of the drug delivery device 1, when the drug delivery device 1 is not in use but serves as a storage container of the medical product. As shown in the following description, the cap 40 is not part of the adaptor of the invention, and is intended to be removed at the time of use of the drug delivery device 1: indeed, when a user wishes to transfer the product from the drug delivery device 1 into another medical device (such as an infusion line, another syringe, etc. . . . ), the cap 40 is removed and replaced by a connector (not shown) allowing the transfer of the medical product from the drug delivery device 1 to said other medical device.

Figure 5:
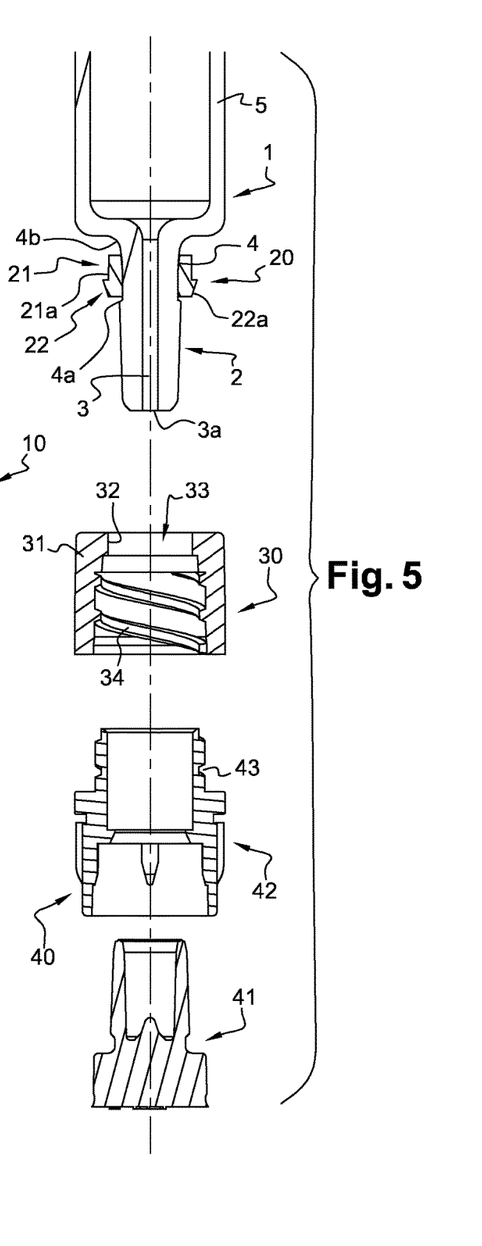
FIG. 5 is a cross sectional view of the drug delivery device and adaptor of FIG. 4, after engagement of the inner ring on the distal tip.
Figure 6:
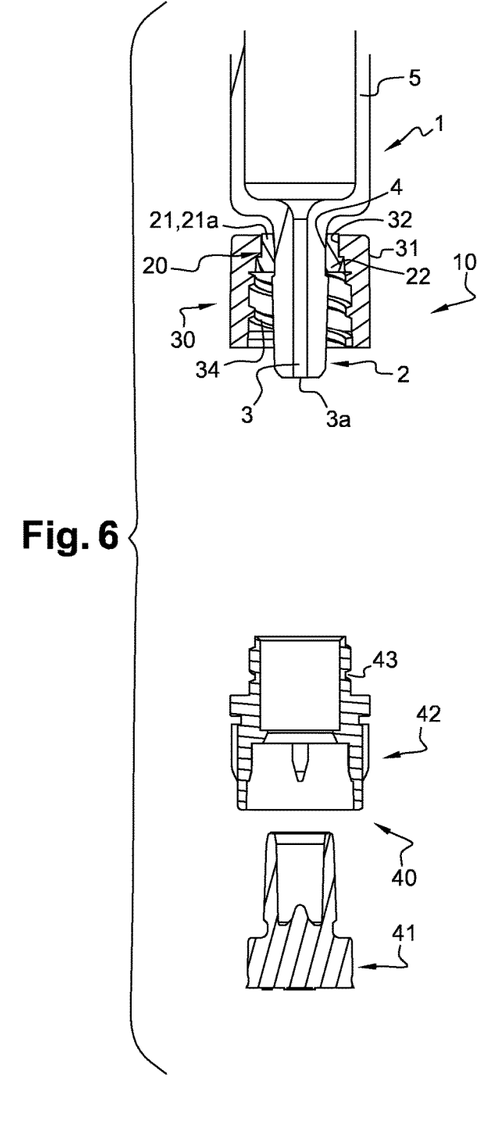
FIG. 6 is a cross section view of the drug delivery device and adaptor of FIG. 4, when the adaptor is mounted on the distal tip.
Figure 7:
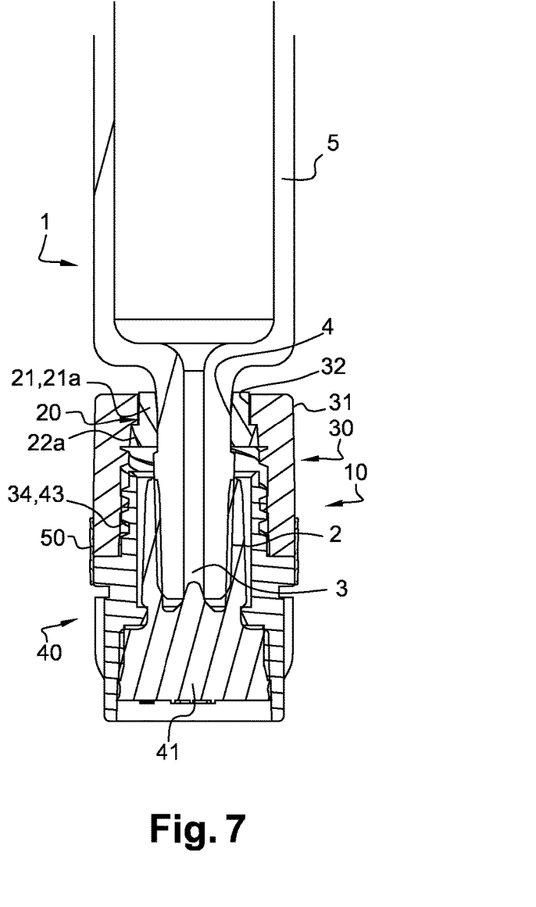
FIG. 7 is a cross section view of the drug delivery device and adaptor of FIG. 4, with a cap closing the distal tip of the drug delivery device.

FIGS. 4-7 show the mounting of the adaptor 10 on the distal tip 2 of the drug delivery device 1 so as to obtain on FIG. 7 the drug delivery device 1 in a storage position. As a consequence, the cap 40 is mounted on the drug delivery device 1 so as to close the distal end 3a of the distal tip 3, the thread 34 thereby forming a connecting means or connection member for connecting the cap 40 to the outer ring 30, by cooperating with a corresponding outer thread 43 provided on the outer wall of the rigid sleeve 42.

As already mentioned above, the cap 40 is not part of the adaptor 10 of the invention and is intended to be replaced with a connector (not shown) provided with a thread capable of cooperating with the thread 34 of the outer ring 30, in view of transferring product from the drug delivery device 1 to another medical device.

On FIG. 4, the inner ring 20 of the adaptor 10 is not engaged yet on the distal tip 2, and the circular wall 21 is not submitted to any strain and is therefore in a rest position.

In a first step, the user engages the inner ring 20 onto the distal tip 2. This step is easy to perform thanks to the distally tapered shape of the outer surface of the distal tip 2 and also thanks to the capability of the circular wall 21 of the inner ring 20 to expand outwardly radially. In particular, the presence of the longitudinal cut 23 of the circular wall 21 facilitates the mounting of the inner ring 20 onto the distal tip 2. On the example shown, the inner ring 20 is engaged on the distal tip 2 beyond distal step 4a of proximal annular groove 4. With reference to FIG. 5, the inner ring 20 is engaged on the distal tip 2 until the inner face 21c of the circular wall 21 faces and is in contact with the annular groove 4 of the distal tip 2.

In embodiments where the distal tip 2 is free of any annular groove, the inner ring 20 may be engaged on said distal tip 2 until the proximal end of the inner ring comes close to the shoulder formed by the distal part of the barrel 5 of the drug delivery device 1.

When the inner ring 20 is engaged on the distal tip 2 and the outer ring 30 is not yet snap-fitted thereon, the proximal tabs 21a of the circular wall 21 may exert a slight radial inward force on the distal tip 2, regardless form the fact that said distal tip 2 is provided with an annular groove or not. Alternatively, these proximal tabs 21a may exert no inward radial force onto the distal tip 2. At this stage, the inner ring 20 is engaged on the distal tip 2 in a releasable way, and the potential radial inward force exerted by the circular wall 21 on the distal tip 2 does not limit the axial movement of the inner ring 20 with respect to the distal tip 2. The inner ring 20 may still be translated with respect to the distal tip 2.

In the example shown, where the distal tip 2 is provided with an annular groove 4 forming a distal abutment 4a for the inner ring 20, the proximal tabs 21a of the circular wall 21 do not exert any radial inward force on the outer face of the annular groove 4 if the outer diameter of the proximal annular groove 4 is less than the inner diameter of the circular wall 21 in a rest position.

Then, the user approaches the outer ring 30 to the distal end of the distal tip 2, engages it thereon and towards the inner ring 20 already in place on the distal tip 2. When the user moves the outer ring 30 in the proximal direction, the inner radial rim 32 comes in contact with the distally tapered outer face 22a of the annular outer rim 22 of the inner ring 20. Thanks to the distally tapered outer face 22a of the annular outer rim 22 and to the inherent flexibility of the material forming the outer ring 30, the inner radial rim 32 overcomes the annular outer rim 22 and gets engaged on the outer face 21d of the circular wall 21. The outer ring 30 is therefore snap-fitted into the inner ring 20.

In embodiments where the distal tip 2 is provided with an annular groove 4 and where the outer diameter of the proximal annular groove 4 is less than the inner diameter of the circular wall 21 in a rest position, the inner radial rim 32 may even cause the annular outer rim 22 to deflect radially inwardly thanks to the capability of the circular wall 21 to be compressed under a pressure exerted on its outer face 21d radially inwardly.

With reference to FIG. 6, in this position, the outer ring 30, via its inner radial rim 32, exerts a radial inwardly pressure on the proximal tabs 21a, in other words on the outer face 21d of the circular wall 21, thereby compressing said circular wall 21. The outer ring 30, via its inner radial rim 32, acts as a compressing means or compression component exerting a centripetal pressure on the circular wall 21 so as to lock the inner ring 20 in translation with respect to the distal tip 2. The radial inward force exerted on the distal tip 2 therefore limits and prevents the axial movement of the inner ring 20, and therefore of the adaptor 10, with respect to said distal tip 2.

In addition, as shown on FIGS. 6 and 7, the inner radial rim 32 is in distal abutment on the annular outer rim 22. The inner radial rim 32 and the annular outer rim 22 therefore forms unreleasable snap-fitting means or engagement of the outer ring 30 into the inner ring 20.

Additionally, in an embodiment not shown, some locking means or locking component may be formed on the outer surface of the distal tip, such locking means being preferably aligned on the longitudinal axis of the drug delivery device. These locking means may have the form of ribs capable of locking the adaptor firmly in rotation thanks to a mechanical abutment with the proximal tabs 21a. These ribs may fit closely within the space existing between two adjacent proximal tabs in order to prevent any rotational movement of the adaptor with respect to the distal tip. Preferably at least two locking means would be required, but the number of the locking means and their distribution on the surface of the distal tip may depend on the number of free spaces existing between two adjacent proximal tabs 21a.

As a consequence, the adaptor 10 is now firmly attached to the distal tip 2, and it may not be disconnected from said distal tip, even if a user tries to pull it out in a direction or the other. The presence of the proximal annular groove 4 on the distal tip 2 increases the fastening resistance of the adaptor 10 onto the distal tip 2 if a user tries to pull it in the distal direction.

As shown in FIG. 7, the passageway 3 of the distal tip 2 may be closed by screwing a cap 40 on thread 34 of the outer ring 30 for storage purposes.

In embodiments, the adaptor 10 may be provided with the cap 40 already screwed in the outer ring 30, before any mounting step of the adaptor 10 onto the distal tip of the drug delivery device. The adaptor 10 may then be provided with a tamper evidence component or tamper evidence means of the removal of the cap 40. For example, a tearable label 50 as shown on FIG. 7 may be stuck bridging the distal part of the outer ring 30 and the proximal part of the cap 40 so as to constitute tamper evidence means of the removal of the cap 40 from the adaptor 10.

For using the drug delivery device 1, the user only needs to remove first the tearable label 50 if present, and then the cap 40 by unscrewing it from the outer ring 30. This step is easy to complete thanks to the secured fixation of the adaptor 10 onto the distal tip 2. In particular, the user knows that the removal of the cap 40 can be done safely and may not cause the adaptor 10 to be separated from the distal tip 2. Once the cap 40 is removed, the user may then screw on thread 34a corresponding outer thread provided on a connector (not shown) in order to proceed to the transfer of the product contained in the drug delivery device to another medical device via the connector.

Again, because of the optimized fixation of the adaptor 10 on the distal tip 2, the connection of the connector to the adaptor 10, and therefore to the distal tip 2 is facilitated.

The adaptor of the invention allows the reliable connection of a connector on the distal tip of a drug delivery device. The risks that the adaptor of the invention be displaced and eventually misplaced on the distal tip of the drug delivery device and that the connector be wrongly connected are greatly limited.

The invention claimed is:

1. An adaptor intended to be mounted on a distal tip of a drug delivery device, said distal tip defining an axial passageway for transfer of a product contained in said drug delivery device, said adaptor having a longitudinal axis A aligned on said axial passageway, the adaptor comprising:
    a connection member for connecting said adaptor to a connector;
    an inner ring releasably engageable on said distal tip, the inner ring comprising a circular wall configured to be outwardly radially expanded under a pressure exerted radially outwardly on an inner face of said circular wall, and configured to be inwardly radially compressed under a pressure exerted radially inwardly on an outer face of said circular wall; and
    a compression component separate from said inner ring and configured to be unreleasably snap-fitted onto said inner ring engaged on said distal tip by proximal movement of said compression component with respect to said inner ring, said compression component being configured to exert a centripetal pressure on said inner ring so as to prevent axial movement of said inner ring with respect to said distal tip, said compression component comprising an outer ring configured to receive at least partly said inner ring, said outer ring comprising an inner radial rim configured to exert a centripetal pressure on said outer face of said circular wall when said compression component is snap-fitted onto said inner ring, said circular wall comprising a longitudinal cut along a portion of a circumference thereof, and said longitudinal cut extending from a proximal end to a distal end of said circular wall.

2. The adaptor according to claim 1, wherein said portion of the circumference of said circular wall is wide enough for defining an empty space between two longitudinal edges of said longitudinal cut, when no pressure is exerted on said circular wall.

3. The adaptor according to claim 2, wherein said portion of the circumference of the circular wall is at least 2 mm wide.

4. The adaptor according to claim 1, wherein said circular wall comprises a distal annular outer rim configured to cooperate with said inner radial rim for unreleasably snap-fitting said compression component onto said inner ring.

5. The adaptor according to claim 1, wherein said connection member is located on the compression component.

6. The adaptor according to claim 1, wherein said connection member comprises a thread provided on an inner wall of said outer ring.

7. A drug delivery device comprising:
   a distal tip defining an axial passageway for transfer of a product contained in said drug delivery device; and
   at least one adaptor configured to be mounted on said distal tip and having a longitudinal axis A aligned on said axial passageway, the adaptor comprising:
      a connection member comprising a thread for connecting said adaptor to a connector;
      an inner ring releasably engageable on said distal tip, the inner ring comprising a circular wall configured to be outwardly radially expanded under a pressure exerted radially outwardly on an inner face of said circular wall, and configured to be inwardly radially compressed under a pressure exerted radially inwardly on an outer face of said circular wall; and
      a compression component separate from said inner ring and configured to be unreleasably snap-fitted onto said inner ring engaged on said distal tip by proximal movement of said compression component with respect to said inner ring, said compression component being configured to exert a centripetal pressure on said inner ring so as to prevent axial movement of said inner ring with respect to said distal tip, said compression component comprising an outer ring configured to receive at least partly said inner ring, said outer ring comprising an inner radial rim configured to exert a centripetal pressure on said outer face of said circular wall when said compression component is snap-fitted onto said inner ring, said circular wall comprising a longitudinal cut along a portion of a circumference thereof, and said longitudinal cut extending from a proximal end to a distal end of said circular wall.

8. An assembly comprising:
   an adaptor configured to be mounted on a distal tip of a drug delivery device, said distal tip defining an axial passageway for transfer of a product contained in said drug delivery device, said adaptor having a longitudinal axis A aligned on said axial passageway, the adaptor comprising:
      a connection member for connecting said adaptor to a connector;
      an inner ring releasably engageable on said distal tip, the inner ring comprising a circular wall configured to be outwardly radially expanded under a pressure exerted radially outwardly on an inner face of said circular wall, and configured to be inwardly radially compressed under a pressure exerted radially inwardly on an outer face of said circular wall; and
      a compression component separate from said inner ring and configured to be unreleasably snap-fitted onto said inner ring engaged on said distal tip by proximal movement of said compression component with respect to said inner ring, said compression component being configured to exert a centripetal pressure on said inner ring so as to prevent axial movement of said inner ring with respect to said distal tip, said compression component comprising an outer ring configured to receive at least partly said inner ring, said outer ring comprising an inner radial rim configured to exert a centripetal pressure on said outer face of said circular wall when said compression component is snap-fitted onto said inner ring, said circular wall comprising a longitudinal cut along a portion of a circumference thereof, and said longitudinal cut extending from a proximal end to a distal end of said circular wall; and
   a connector connected to said connection member of said adaptor.

9. The assembly according to claim 8, wherein said adaptor further comprises a tamper evidence component for removing the connector from the adaptor.

10. The drug delivery device according to claim 7, wherein the distal tip is made of glass.

11. The drug delivery device according to claim 7, wherein the distal tip is conical and distally tapered.

12. The drug delivery device according to claim 7, wherein the distal tip comprises an annular groove configured to receive said inner ring when said inner ring is engaged on said distal tip.

13. A method for mounting an adaptor on a distal tip of a drug delivery device, wherein said distal tip defines an axial passageway for transfer of a product contained in said drug delivery device, said adaptor being configured to be mounted on the distal tip and having a longitudinal axis A aligned on said axial passageway, the adaptor comprising:
   a connection member for connecting said adaptor to a connector;
   an inner ring releasably engageable on said distal tip, the inner ring comprising a circular wall configured to be outwardly radially expanded under a pressure exerted radially outwardly on an inner face of said circular wall, and configured to be inwardly radially compressed under a pressure exerted radially inwardly on an outer face of said circular wall; and
   a compression component separate from said inner ring and configured to be unreleasably snap-fitted onto said inner ring engaged on said distal tip by proximal movement of said compression component with respect to said inner ring, said compression component being configured to exert a centripetal pressure on said inner ring so as to prevent axial movement of said inner ring with respect to said distal tip, said compression component comprising an outer ring configured to receive at least partly said inner ring, said outer ring comprising an inner radial rim configured to exert a centripetal pressure on said outer face of said circular wall when said compression component is snap-fitted onto said inner ring, said circular wall comprising a longitudinal cut along a portion of a circumference thereof, and said longitudinal cut extending from a proximal end to a distal end of said circular wall,
   the method comprising:
      slidingly engaging the inner ring onto the distal tip; and
      snap-fitting the compression component onto the inner ring by proximal movement of said compression component with respect to said inner ring.

14. The method according to claim 13, wherein the inner ring is slidingly engaged on the distal tip until the inner ring is received into an annular groove.

* * * * *